United States Patent [19]

Buysch et al.

[11] Patent Number: 5,266,716
[45] Date of Patent: Nov. 30, 1993

[54] PROCESS FOR THE SPLITTING OF POLYCARBONATES

[75] Inventors: Hans-Josef Buysch; Norbert Schön; Steffen Kühling, all of Krefeld, Fed. Rep. of Germany

[73] Assignee: Bayer Aktiengesellschaft, Leverkusen, Fed. Rep. of Germany

[21] Appl. No.: 988,048

[22] Filed: Dec. 9, 1992

[30] Foreign Application Priority Data

Dec. 19, 1991 [DE] Fed. Rep. of Germany ....... 4141954

[51] Int. Cl.$^5$ .................. C07C 69/96; C07C 27/26
[52] U.S. Cl. .................... 558/260; 558/270; 558/274; 558/275; 558/277; 568/858
[58] Field of Search .......... 558/274, 275, 277, 260, 558/270; 568/858

[56] References Cited

U.S. PATENT DOCUMENTS 2,776,323  1/1957  Toland et al. .......... 568/858
4,252,737  2/1981  Krimm et al. .......... 558/274
5,210,268  5/1993  Fukuoka et al. .......... 558/277

FOREIGN PATENT DOCUMENTS 0937550  9/1963  United Kingdom .

*Primary Examiner*—Jose' G. Dees
*Assistant Examiner*—Dwayne C. Jones
*Attorney, Agent, or Firm*—Joseph C. Gil; Aron Preis

[57] ABSTRACT

A process for the continuous splitting of polycarbonates into dihydroxy compounds and carbonic acid esters is disclosed. Accordingly there are reacted in a distillation column a polycarbonate resin and a monohydroxy compound in the presence of a transesterification catalyst. The polycarbonate, in molten form or as a solute, is continuously fed into the upper part of the column and the monohydroxy compound in vapor phase is continuously fed into the lower part of the column. The resulting carbonic acid ester and dihydroxy compounds are continuously being removed from the column. The process is eminently suitable for the recycling of polycarbonate waste.

5 Claims, No Drawings

PROCESS FOR THE SPLITTING OF POLYCARBONATES

FIELD OF THE INVENTION

The invention relates to polycarbonates and more particularly to a process useful for splitting waste polycarbonate resins to dihydroxy compounds and carbonic acid esters.

SUMMARY OF THE INVENTION

A process for the continuous splitting of polycarbonates into dihydroxy compounds and carbonic acid esters by catalytic transesterification with monohydroxy compounds is disclosed. Accordingly, polycarbonate resin in the form of a melt or a solution in a suitable solvent is reacted with 50 to 15,000 mol % monohydroxy compound and in the presence of 0.0001 to 20 mol-% of a transesterification catalyst said percent being relative to the molar amount of carbonate units in the polycarbonate. The polycarbonate is fed into the upper part of a distillation column and the monohydroxy compound is introduced in countercurrent into the lower part of the distillation column in the vapor phase. A stream of carbonic acid ester is removed at the head of the distillation column and a stream of dihydroxy compounds is removed at the foot of the distillation column.

BACKGROUND OF THE INVENTION

It is known that polycarbonates can be split with hydroxy compounds into dialkyl carbonates and dihydroxy compounds. This process requires long reaction and holding times, during which product damage cannot be ruled out, and is carried out, in batches (DAS 1,155,452).

By contrast, the process according to the invention can be continuously carried out simply and with high yields. One particular advantage is that the transesterification can be taken to high yields in a single step or may even be carried out quantitatively in dependence upon the mode of operation of the transesterification column with simultaneous separation of the reaction products.

DETAILED DESCRIPTION OF THE INVENTION

The polycarbonates to be split are melted in known manner, for example in an extruder. The polycarbonates to be split may also be dissolved via the melt in the above-mentioned extrusion process and also in known mixing units, tank reactors, etc.

Suitable solvents are solvents which are inert under the reaction conditions and which dissolve the polycarbonates and the dihydroxy compounds formed in the esterification reaction under the reaction conditions and of which the boiling point is at least comparable with and, better still, above that of the hydroxy compound used for the transesterification.

Solvents such as these are, for example, hydrocarbons, such as octane, dodecane, isooctane, isododecane, decalin, toluene, xylenes, cumene, cymol, trimethyl benzenes, tetramethyl benzenes, diisopropyl benzenes, tetralin, naphthaline, bisphenyl; ethers, such as dibutyl ether, dioxane, dimethyl diglycol, diethyl triglycol, dimethyl tetraglycol, anisole, phenylbutyl ether, methoxytoluenes, dimethoxybenzenes, diphenyl ether; halogenated hydrocarbons, such as chlorobenzene, dichlorobenzene, bromobenzene, dibromobenzenes, chloronaphthalenes, chlorotoluenes, chloroxylenes, chlorocumenes, amides, such as dimethyl acetamide, N-acetyl morpholine, N,N-dimethyl benzamide.

The quantity of solvent used is between 1 and 20 times, preferably between 2 and 15 times and, more preferably, between 3 and 12 times the quantity of polycarbonate.

The monohydroxy compounds suitable for splitting the polycarbonates in accordance with the invention are aliphatic $C_{1-30}$ monoalcohols, cycloaliphatic $C_{3-10}$ monoalcohols and araliphatic $C_{7-30}$ monoalcohols. Suitable aliphatic monoalcohols are primary and secondary monoalcohols, suitable cycloaliphatic monoalcohols are secondary monoalcohols and suitable araliphatic monoalcohols are, again, primary and secondary monoalcohols.

Suitable monohydroxy compounds are, for example, methanol, ethanol, propanol, isopropanol, butanol, secondary butanol, isobutanol, pentanols, hexanols, octanols, decanols, undecanols, dodecanols, stearyl alcohol, cyclopentanol, cyclohexanol, cyclooctanol, cyclododecanol, benzyl alcohol, phenyl ethanol, preferably methanol, ethanol, propanol, butanol, cyclohexanol, benzyl alcohol. Methanol and ethanol are particularly preferred.

The above-mentioned monohydroxy compounds suitable for the splitting of polycarbonates in accordance with the invention may be added together with the solvent before dissolution of the polycarbonate in quantities of 50 to 1,000 mol-% per mol carbonate units in the polycarbonate. The monohydroxy compounds may also be used instead of the solvents for dissolving the polycarbonate. In this case, the monohydroxy compound is used in a quantity of 200 to 15,000 mol-%, preferably in a quantity of 300 to 5,000 mol-% and, more preferably, in a quantity of 400 to 3,000 mol-%.

In both cases, addition of the monohydroxy compound is used both for dissolving the polycarbonate and also for partial degradation thereof before and during introduction into the upper part of the distillation column.

Accordingly, the present invention also relates to an extension of the process according to the invention which is characterized in that the monohydroxy compounds suitable for the splitting of polycarbonates in accordance with the invention are additionally or alternatively used as the polycarbonate solvent in quantities of 50 to 1,000 mol-% per mol carbonate unit in the polycarbonate in the case of additional use or in quantities of 200 to 15,000 mol-% per mol carbonate unit in the polycarbonate where the monohydroxy compound is used as sole polycarbonate solvent.

The additional use or sole use of the monohydroxy compounds to be used for splitting polycarbonates in accordance with the invention as polycarbonate solvent is particularly recommended when the polycarbonate is soluble in the hydroxy compound under the reaction conditions or passes into solution after partial degradation. This may readily be determined in each individual case by preliminary tests.

In one particular variant of the polycarbonate degradation process according to the invention, a monohydroxy compound having a higher boiling temperature than the monohydroxy used for splitting is used as the polycarbonate solvent. It is advisable to adopt this procedure when the higher boiling monohydroxy compound has a better dissolving power for the polycarbonate, dissolving power in this context also being understood to include the partial degradation of the polycarbonate. It is possible in this way to considerably accelerate the transesterification process in the column. The higher boiling monohydroxy compound is used in a quantity of 10 to 3,000 mol-%, preferably in a quantity of 50 to 2,500 mol-% and, more preferably, in a quantity of 100 to 2,000 mol-% per mol carbonate unit in the quantity by weight of polycarbonate to be split.

Accordingly, the present invention also relates to an extension of the process according to the invention which is characterized in that a monohydroxy compound which boils at a higher temperature, preferably at least 5° C. higher, than the monohydroxy compound used for splitting polycarbonates in accordance with the invention in the distillation column is used as the polycarbonate solvent, 10 to 3,000 mol-% of the higher boiling monohydroxy compound being used per mol carbonate unit in the polycarbonate.

Suitable relatively high boiling monohydroxy compounds are, in principle, those already mentioned for the splitting of polycarbonates in accordance with the invention, except for those which have the lowest boiling point and which, accordingly, can only be used for the splitting of polycarbonates in accordance with the invention in the distillation column where this procedure is adopted.

In addition, phenols may also be used as the relatively high-boiling monohydroxy compounds. In addition to phenol itself, suitable phenols are, for example, cresol, methoxyphenol, chlorophenol and isopropylphenol.

In addition, the use of phenols as the relatively high boiling monohydroxy compounds has the following advantage: If phenol is used as an additional hydroxy compound, for example in the splitting of bisphenol A polycarbonate with methanol in bisphenol A and dimethyl carbonate, rapid preliminary degradation of the polycarbonate is initiated if the polycarbonate is dissolved in phenol in the presence of the catalyst. It is thus possible to prepare highly concentrated, low-viscosity solutions of partly degraded polycarbonate which guarantee a better volume of the time yield in the transesterification reaction. Simple separation of the dialkyl carbonate is guaranteed by virtue of the large differences in boiling point. In addition, the bisphenol A formed can be recovered from the sump in crystalline form as the known 1:1 adduct with phenol. In this way, it is also possible for example to couple the process with any bisphenol A production present which can take over the further purification and working up of the bisphenol A adduct to bisphenol A in known manner.

Suitable combinations of monohydroxy compounds of polycarbonate donor according to the invention/polycarbonate solvent according to the invention include methanol/ethanol, methanol/butanol, methanol/hexanol, methanol/phenol, methanol/cresol, methanol/methoxyphenol, ethanol/hexanol, ethanol/octanol, ethanol/decanol, ethanol/ phenol, ethanol/chlorophenol, ethanol/isopropylphenol, butanol/octanol and butanol/phenol.

In the most simple case, the distillation column used for the process according to the invention is an isothermally heated tube filled with packing elements typically used for distillation. The transesterification steps are completed surprisingly quickly in the tube so that considerable quantities of carbonic acid ester distill off overhead, even with a relatively short column of this type. However, the column may also contain a stripping section operating at elevated temperature at its lower end in which the monohydroxy compound is substantially or completely separated from the dihydroxy compound flowing down and returned to the transesterification part of the column.

In addition, the upper part of the column may be formed by a rectifying section operating at a relatively low temperature to complete the separation of gaseous monohydroxy compound and carbonic acid ester from relatively high-boiling components, such as the solvent for example, and thus to remove a high-percentage or pure mixture of monohydroxy compound and carbonic acid ester at the head of the column.

Energy may be supplied via the monohydroxy compound introduced into the column in vapor form and/or via the sump evaporator. The monohydroxy compound may even be introduced in liquid form, in which case energy must be supplied via the evaporator. In the first case, the diameter of the column in the middle section where most of the transesterification takes place may advantageously be enlarged to four times the diameter of the remaining parts of the column. In the second case, the enthalpy of evaporation for the monohydroxy compound must be transported through the stripping section where it leads to a high gas and liquid load. This results in widening of the column in the stripping section to guarantee the separations intended to take place there. The widening and length of the stripping section depends upon the selected column fittings in the stripping section which can be laid out by the expert.

Since two molecules of monohydroxy compound can be replaced by one molecule of carbonic acid ester during the transesterification in the gas phase, a reduction in cross section by a factor of up to 2 can be an advantage to keep the gas flow rate in the middle part of the column constant.

Accordingly, the column can be both isothermally heated and—preferably—equipped with one or more temperature zones different from the main section to produce a temperature gradient with downwardly decreasing values.

The filling or packing elements may be any of those typically used for distillation which are described, for example, in Ullmann's Encyclopadie der technischen Chemie, 4th Edition, Vol. 2, pages 528 et seq. or in the brochures published by manufacturers of the equipment in question. Examples of suitable packing elements are Raschig or Pall rings, Berl-Intalex or Torus saddles, Interpack elements of various materials, such a glass, stoneware, porcelain, carbon, stainless steel and plastic, which—particularly where metal is used—may be processed like woven or knitted fabrics. Preferred packing and filling elements have a large surface and guarantee thorough wetting and an adequate residence time of the liquid. They include, for example, Pall and Novolax rings, Berl saddles, BX Packs, Montz-Pak, Mellapak, Melladur, Kerapak and CY Packs.

However, not only packed columns but also columns with fixed fittings are suitable for the process according to the invention. Fixed fittings are understood to be bubble plates or valve plates combining long residence times with a good exchange of material.

However, other plate columns, for example sieve plate columns, bubble plate columns, valve plate columns, tunnel plate columns and centrifugal plate columns, which are available in various forms, are also generally suitable.

Catalysts suitable for the splitting of polycarbonates in accordance with the invention are known from the literature (see, for example, DDR patents 45,600 and 46,363, DE-AS 1,155,452 and JA 61/27 203A). Suitable catalysts include hydrides, oxides, hydroxides, alcohols, amides or salts of alkali metals, such as lithium, sodium, potassium, rubidium and cesium, preferably salts of lithium, sodium and potassium and, more preferably, salts of sodium and potassium. Salts of alkali metals are those of organic and inorganic acids, for example acetic acid, propionic acid, butyric acid, benzoic acid, stearic acid, carbonic acid, hydrochloric acid, HBr, HI, nitric acid, $H_2SO_4$, HF, phosphoric acid, boric acid, tin acids and antimony acids.

Preferred alkali metal catalysts are alkali metal oxides, hydroxides, alcoholates, acetates, propionates, benzoates, carbonates and hydrogen carbonates. Particularly alkali metal catalysts are the alkali metal hydroxides, alcoholates, acetates, benzoates and carbonates.

The alkali metal,catalysts are used in quantities of 0.0001 to 20 mol-%, preferably in quantities of 0.001 to 10 mol-% and, more preferably, in quantities of 0.005 to 5 mol-% per mol carbonate unit in the polycarbonate to be split.

The alkali metal catalysts may optionally be used in combination with complexing agents, such as for example crown ethers, polyethylene glycols or bicyclic nitrogen containing kryptands.

Dibenzo-18-crown-6 is an example of a suitable crown ether while 1,9-dimethyl-1,9-diazadibenzo-18-crown-6 is an example of a suitable nitrogen-containing kryptand.

The complexing agents are used in quantities of 0.1 to 200 mol-% and preferably in quantities of 1 to 100 mol-% per mol alkali metal compound.

Other catalysts for the splitting of polycarbonates in accordance with the invention are nitrogen-containing bases, such as for example secondary and tertiary amines, such as triethyl amine, tributyl amine, methyl dibenzyl amine and dimethyl cyclohexyl amine, diazabicycloundecane or diazabiscyclononane.

The nitrogen-containing bases are used in quantities of 0.001 to 20 mol-%, preferably in quantities of 0.005 to 10 mol-% and, more preferably, in quantities of 0.01 to 3 mol-% per mol carbonate unit in the polycarbonate to be split.

Other suitable catalysts for the splitting of polycarbonates in accordance with the invention are complexes or salts or compounds of magnesium, calcium, barium, zinc, tin, titanium or zirconium. Examples of such systems are tin methoxide, dimethyl tin, dibutyl tin oxide, dibutyl tin dilaurate, tributyl tin hydride, tributyl tin chloride, tin (II) ethyl hexanoate, zirconium alkoxides (methyl, ethyl, butyl), zirconium(IV) halides (F, Cl, Br, I), zirconium nitrates, zirconium acetyl acetonate, titanium alkoxides (methyl, ethyl, isopropyl), titanium acetate and titanium acetyl acetonate.

These catalysts are used in quantities of 0.0001 to 20 mol-%, preferably in quantities of 0.001 to 10 mol-% and, more preferably, in quantities of 0.005 to 5 mol-% per mol carbonate unit in the polycarbonate to be split.

The catalysts to be used are added in bulk either to the polycarbonate melt or to the polycarbonate solution. Where a monohydroxy compound is used as the polycarbonate solvent, alkali metal alcoholates or even alkali metal phenolates may be formed in situ where alkali metal catalysts are used. The catalysts to be used for the splitting of polycarbonates may also be separately added to the polycarbonate melt or to the polycarbonate solution via the head of the distillation column to be used in the form of a solution in the monohydroxy compound intended for the splitting of the polycarbonates. In this case, too, alkali metal alcoholates may be produced in situ where alkali metal catalysts are used.

In cases where a heterogeneous catalyst which is sparingly soluble or insoluble in the reactants is used, it may even be introduced beforehand in admixture with the packing elements of the distillation column or as a bed on built in column plates or may be built into the column as a pack.

The distillation column to be used in accordance with the invention is preferably operated by introducing the polycarbonate in the form of a melt or solution and optionally the catalyst in bulk or in solution into the upper half and preferably into the upper third of the column.

The polycarbonate preferably is at the same temperature which prevails at the level at which it is introduced into the column.

The monohydroxy compound used for the splitting of polycarbonates is introduced into the lower half of the column and preferably above any stripping zone present.

The monohydroxy compound intended for the splitting of polycarbonates is preferably introduced in vapor form. If it is introduced in liquid form, it must be evaporated in the sump evaporator, as already mentioned.

The carbonic acid ester is removed and condensed at the head of the column, preferably after passing through a rectifying section. In general, it still contains fractions of the monohydroxy compound present in the system. A solution or melt of the dihydroxy compound(s), on which the polycarbonate is based, is discharged from the sump of the column under carefully established conditions and may be worked up and purified by known methods, for example by distillation and/or crystallization, or otherwise.

The temperature in the column is in the range from 50° to 200° C., preferably in the range from 60° to 190° C. and, more preferably, in the range from 70° to 170° C. Any temperature gradient applied is within the temperature range indicated and increases from the head to the sump of the column.

In general, the reaction on which the process according to the invention is based is carried out under normal pressure although it may also be carried out at a slightly elevated pressure of up to about 5 bar, preferably of up to 4 bar and, more preferably, of up to 3 bar or under a reduced pressure of down to 50 mbar, preferably down to 100 mbar and, more preferably, down to 200 mbar. The azeotrope to be removed, for example, at the head of the column may be influenced by carrying out the reaction at pressures differing from normal pressure, as known to the expert.

The volume/time load of the column is between 0.1 and 5.0 g of the total quantity of reactants per ml effective column volume per hour, preferably between 0.2 and 4.0 g/ml/h and, more preferably, between 0.3 and 3.0 g/ml/h. The effective column volume is the space occupied by the column pack or the space in which fixed fittings are accommodated.

Polycarbonates in the context of the invention are generally polycarbonates based on aliphatic and/or araliphatic and/or aromatic dihydroxy compounds of the type which are, and can be, used on an industrial scale.

Aliphatic dihydroxy compounds are, for example, ethylene glycol, 1,2- and 1,3-propylene glycol, neopentyl glycol, hexane-1,6-diol, cyclohexane dimethanol, 2,2,5-trimethylhexane-1,6-diol, dodecane-1,2-diol, trimethylol propane monoallyl ether, dianhydrosorbitol, diglycol, triglycol, tetraglycol or mixtures of these diols, preferably neopentyl glycol and hexanediol.

Araliphatic dihydroxy compounds are, for example, xylylene diols, the ethoxylation products of bisphenols, such as hydroquinone, resorcinol, pyrocatechol, bisphenol A, dihydroxydiphenyl, dihydroxydiphenyl sulfone, bisphenol F, bisphenol Z and other typically used bisphenols or mixtures of these diols, preferably the ethoxylation products of 2,2-bis-(4-hydroxyphenyl)-propane.

Aromatic dihydroxy compounds are, for example, dihydroxybenzenes, dihydroxybiphenyl, dihydroxydiphenyl ether, dihydroxydiphenyl sulfide, dihyroxydiphenyl sulfone, dihydroxydiphenyl methane (bisphenol F) dihydroxydiphenyl ethane, dihydroxydiphenyl propane (bisphenol A) dihydroxydiphenyl cyclohexane (bisphenol z), 3,3,5-trimethyl-1,1-(dihydroxydiphenyl)-cyclohexane, $\alpha,\alpha'$-(dihydroxyphenyl)diisopropyl benzenes, dihydroxybenzophenone or mixtures of the aromatic dihydroxy compounds, preferably bisphenol A, bisphenol 2, dihydroxydiphenyl methane and 3,3,5-trimethyl-1,1-(dihydroxydiphenyl)-cyclohexane. Bisphenol A is particularly preferred.

The polycarbonates to be split in accordance with the invention are known from the literature (see, for example, the book by H. Schnell entitled "Chemistry and Physics of Polycarbonates", Interscience Publishers, New York, 1964).

The polycarbonates to be split have molecular weights Mw (weight averages, as determined for example by gel permeation chromatography) in the range from 5,000 to 200,000 and preferably in the range from 10,000 to 80,000. The molecular weights may also be determined in known manner by measurement of the relative viscosity in $CH_2Cl_2$ at 25° C. and at a concentration of 0.5% by weight. The polycarbonates to be split are preferably aromatic thermoplastic polycarbonates which are preferably produced from at least one of the following diphenols: 4,4'-dihydroxydiphenyl, 2,2-bis-4-hydroxyphenyl)-propane (bisphenol A), 2,4-bis-4-hydroxyphenyl)-2-methyl butane, 1,1-bis-(4-hydroxyphenyl)-cyclohexane, $\alpha,\alpha'$-bis-(4-hydroxyphenyl)-p-diiso-propyl benzene, 2,2-bis-(3-chloro-4-hydroxyphenyl)-propane, 2,2-bis-(3,5-dichloro-4-hydroxyphenyl)-propane, 2,2-bis-(3,5-dibromo-4-hydroxyphenyl)-propane and 1,1-bis-(4-hydroxyphenyl)-3,3,5-trimethyl cyclohexane.

The polycarbonates to be split in accordance with the invention may also be branched in known manner by the incorporation of trifunctional or more than trifunctional compounds. In the splitting of the polycarbonates in accordance with the invention these trifunctional or more than trifunctional compounds are collected together with the dihydroxy compounds in the sump of the distillation column and optionally isolated by crystallization.

Where they are monophenols, the chain terminators released from the polycarbonates to be split in accordance with the invention are also collected in the sump of the distillation column and optionally isolated in known manner. Where aliphatic or cycloaliphatic monoalcohols are incorporated as chain terminators in the polycarbonates to be split, they are removed as monocarbonate diesters via the head of the distillation column.

Choosing between introducing the polycarbonate as a melt and as a solute in the context of the present process depends on the molecular weight of the polycarbonate and on the dihydroxy compounds from which the polycarbonates are synthesized.

Polycarbonates capable of being metered as melts are preferably polycarbonates based on aliphatic, cycloaliphatic and/or araliphatic dihydroxy compounds or on mixtures of these dihydroxy compounds with diphenols.

Purely aromatic polycarbonates of diphenols as the dihydroxy component generally have high melting temperatures and are therefore mainly introduced in solution into the splitting process according to the invention.

Polycarbonates capable of being metered as melts are, in particular, polycarbonates of hexane-1,6-diol, diglycol, propane-1,3-diol, neopentyl glycol, bisoxyethyl bisphenol A, cyclohexane dimethanol, ethylene glycol and copolycarbonates of these diols with one another and with diphenols, such as bisphenol A, dihydroxybiphenyl, 1,1-bis-(4-hydroxy-phenyl) -cyclohexane and 1,1-bis-(4-hydroxyphenyl)-3,3,5-trimethyl cyclohexane.

The process according to the invention for splitting polycarbonates may be used on a general basis for the various polycarbonate molding compounds. However, its primary function is not to synthesize dihydroxy compounds and carbonic acid esters in this way, but mostly to chemically split otherwise unusable polycarbonate molding compounds, i.e. for example waste or scrap accumulating in the production of moldings, unusable moldings, polycarbonate refuse, etc. Into monomeric components which are easy to purify and, accordingly, can be reused for the production of polycarbonates or for other purposes: the dihydroxy compounds, for example, for the production of epoxy resins or polyurethanes and the carbonic acid esters as solvents or for syntheses in organic chemistry. Accordingly, the polycarbonates to be split in accordance with the invention may contain the usual additives, such as mineral fillers, such as silica flour, glass powder, glass fibers, stabilizers, UV stabilizers, lubricants, pigments, dyes, also polymeric blending partners, such as for example vinyl polymers of styrene, acrylonitrile and butadiene.

The additives insoluble in the polycarbonate melt or in the polycarbonate solution are removed by filtration, centrifugation or sedimentation before the melt or solution is introduced into the transesterification column. The additives soluble in the polycarbonate melt or in the polycarbonate solution may be removed from the dihydroxy compounds obtained by distillation or crystallization.

Coloring impurities present in the polycarbonate used may be removed not only by distillation or crystallization, but also by adsorptive purification techniques, for example on active carbon, kieselguhr, cellulose or zeolites. These adsorptive purification processes may be carried out both with the polycarbonate solution before splitting in accordance with the invention and also with the solutions of the dihydroxy compounds collecting in the sump of the distillation column. Accordingly, the process according to the invention for splitting polycarbonates is eminently suitable for the recycling of polycarbonate waste.

The invention is further illustrated but is not intended to be limited by the following examples in which all parts and percentages are by weight unless otherwise specified.

EXAMPLES

Example 1

Approx. 170 ml/h of a 10% solution of bisphenol A polycarbonate, molecular weight approx. 28,000, in o-dichlorobenzene containing 1% by weight, based on polycarbonate, dibutyl tin oxide as catalyst are delivered to the first plate of a 10-plate bubble plate column while approx. 100 ml/h methanol in vapor for at 90° to 95° C. are introduced below the 10th plate. The column is surrounded by a heating jacket through which oil heated to 80°-85° C. flows. A mixture of methanol and dimethyl carbonate distills off from the head of the column through a short packed column (herein head product) while a solution of bisphenol A in o-dichlorobenzene is discharged at the foot of the column after passing through a short stripping section which is also heated at 80° to 85° C. (herein bottom product).

362 g of head product containing 29 g dimethyl carbonate in addition to methanol and 8 g o-dichlorobenzene and 810 g colorless bottom product containing 72 g bisphenol A in o-dichlorobenzene in addition to a little methanol are obtained after a reaction time of about 4 hours. Dimethyl carbonate can readily be removed from the head product by distillation and the methanol can be returned to the reaction. After concentration of the sump product, bisphenol A crystallizes out in the form of colorless crystals. Polycarbonate is no longer present. The conversion and yield are substantially complete.

Example 2

Example 1 is repeated under the same conditions, 100 ml/h of the 10% bisphenol A polycarbonate solution and 210 ml/h methanol being introduced into the column. 335 g bottom product containing 33 g bisphenol A and 518 g head product containing 13 g dimethyl carbonate are obtained after 3 h. The conversion and yield are substantially complete.

Comparison Example 1 (DAS 1,155,452)

254 g granulated bisphenol A polycarbonate, molecular weight approx. 28,000, 0.5 g NaOH and 160 g methanol were boiled under reflux. After 10 h, the reaction was over and the mixture was separated by distillation, too little dimethyl carbonate distilling over. Accordingly, more methanol was added until no more dimethyl carbonate distilled over. The total reaction time was 19 h. 82 g dimethyl carbonate were distilled over. 179 g brownish crystals were obtained from the brown bottom product by recrystallization from toluene.

Comparison Example 2

1000 g of a 10% solution of bisphenol A polycarbonate, molecular weight approx. 28,000, in o-dichlorobenzene were introduced into a tube with a length of 80 cm and a diameter of approx. 5 cm, 1 g dibutyl tin oxide and 50 g methanol were added and, after heating to 90°-100° C., 10-15 g/h methanol were introduced through a bottom frit. The distillate passing over was collected. After 21 h, the reaction was over. Approx. 34 g dimethyl carbonate were obtained in the distillate. The bottom product was a brown solution containing approx. 35 g bisphenol A. After working up, bisphenol A was obtained in the form of brown crystals.

Example 3

The procedure is as in Example 1 except that 300 ml/h of the polycarbonate solution and 180 ml/h methanol are introduced. After 4 h, 127 g bisphenol A were obtained in the bottom product and 50 g dimethyl carbonate in the head product, the conversion and yield being substantially complete.

Example 4

0.15% by weight potassium hydroxide, based on the polycarbonate, were added at 150° C. to a 40% solution of polycarbonate, molecular weight 28,000, in phenol and the resulting solution was pumped immediately afterwards at a rate of approx. 200 g/h into the head of a 1.5 m long laboratory column 28 mm in diameter which was filled with glass Raschig rings and approx. 100 g/h methanol in vapor form were introduced at the bottom of the column above a small stripping section which was heated to 130°-135° C. The effective part of the column had a temperature gradient of about 90° to 70° C. After a near-equilibrium state had been established in the column, a quantity of 743 g of a clear water-light bottom product was obtained after 4 h and began rapidly to crystallize on cooling. By heating to 41° C., phenol/bisphenol A adduct was obtained and was filtered off. The adduct was largely freed from phenol by desorption in vacuo, the remainder being separated off by boiling in toluene. A colorless pure bisphenol A was obtained in a quantity of 260 g, i.e. 92% of the theoretical. The phenolic mother liquor still containing a little bisphenol A was returned to the transesterification reaction. A distillate containing only traces of phenol in addition to methanol and dimethyl carbonate (111 g) distilled over at the head of the column. The traces of phenol were easily removed. The conversion and selectivity are substantially complete.

Example 5

The procedure is as in Example 4, except that approx. 350 g/h of the 40% polycarbonate solution containing 0.15% by weight KOH, based on polycarbonate, are delivered to the column heated at 140° to 150° C. and approx. 200 g/h methanol vapor were introduced. 934 g of a colorless bottom product containing 490 g bisphenol A and a phenol-containing head product containing 180 g dimethyl carbonate were obtained after 4 h at a column temperature of 150° C.

Example 6

About 500 g/h of a 40% polycarbonate solution containing 1% by weight octyl-stannic-acid, based on polycarbonate, are delivered to the first plate of a 10-plate bubble plate column with a diameter of 5 cm. surrounded by a heating jacket, heated at 150° and equipped at the ground with a rotation vaporizer which is maintained at 170° C. by a thermostat. To the polycarbonate solution 200 g/h methanol vapor were introduced from below via a vaporizer which is maintained at 150° C. 500-510 g bottom product containing 176-180 g bisphenol-A, and 198-203 g head product containing 69-70 g dimethyl carbonate are obtained per hour. Yield and selection are practically quantitative.

Although the invention has been described in detail in the foregoing for the purpose of illustration it is to be understood that such detail is solely for that purpose and that variations can be made therein by those skilled in the art without departing from the spirit and scope of the invention except as it may be limited by the claims.

What is claimed is:

1. A process for the continuous splitting of polycarbonates into dihydroxy compounds and carbonic acid esters comprising
   (i) reacting in a distillation column a polycarbonate resin and 50 to 15,000%, relative to the molar amount of carbonate units in said polycarbonate, of a monohydroxy compound in the presence of 0.0001 to 20%, relative to the molar amount of carbonate units in said polycarbonate, of a transesterification catalyst, said polycarbonate being continuously fed into the upper part of said column and said monohydroxy compound in vapor phase being continuously fed into the lower part of said column, said polycarbonate being in molten form or as a solute in a suitable solvent and
   (ii) continuously removing from the top of said column a stream of carbonic acid ester, and
   (iii) continuously removing from the bottom of said column a stream of dihydroxy compounds.

2. The process of claim 1 wherein said solvent has a boiling temperature which is higher than the monohydroxy compound.

3. The process of claim 2 wherein said suitable solvent is a monohydroxy compound.

4. A process as claimed in claim 1, characterized in that the monohydroxy compounds suitable for the splitting of polycarbonates in accordance with the invention are additionally or alternatively used as polycarbonate solvent in quantities of 50 to 1,000 mol-% per mol carbonate unit in the polycarbonate in the case of the additional use or in quantities of 200 to 15,000 mol-% per mol carbonate unit in the polycarbonate where the monohydroxy compound is used as sole polycarbonate solvent.

5. A process as claimed in claim 1, characterized in that a monohydroxy compound which boils at a higher temperature that the monohydroxy compound used for the splitting of polycarbonates in accordance with the invention in the distillation column is used as the polycarbonate solvent, 10 to 3,000 mol-% of the higher boiling monohydroxy compound being used per mol carbonate unit in the polycarbonate.

* * * * *